United States Patent [19]

Pederson et al.

[11] Patent Number: 4,899,759
[45] Date of Patent: Feb. 13, 1990

[54] FLOW-THROUGH RESISTIVITY CELL

[75] Inventors: Brian D. Pederson, St. Paul; Bruce A. Tockman, Minneapolis, both of Minn.

[73] Assignee: Cardiac Pacemakers, Inc., St. Paul, Minn.

[21] Appl. No.: 297,664

[22] Filed: Jan. 17, 1989

[51] Int. Cl.$^4$ ............................................... A61B 5/02
[52] U.S. Cl. ..................................... 128/693; 128/734
[58] Field of Search ............................... 128/691–693, 128/713, 734, 635, 637

[56] References Cited

U.S. PATENT DOCUMENTS

| | | | |
|---|---|---|---|
| 3,730,171 | 5/1973 | Namon . | |
| 3,871,359 | 3/1975 | Pacela . | |
| 4,380,237 | 4/1983 | Newbower | 128/693 |
| 4,484,582 | 11/1984 | Rottenberg et al. | 128/691 X |
| 4,548,211 | 10/1985 | Marks | 128/693 X |
| 4,572,206 | 2/1986 | Geddes et al. | 128/692 |
| 4,600,495 | 7/1986 | Fogt | 128/635 X |
| 4,674,518 | 6/1987 | Salo | 128/695 |

Primary Examiner—Angela D. Sykes
Attorney, Agent, or Firm—Haugen and Nikolai

[57] ABSTRACT

A resistivity cell formed integrally with or attached to the proximal end of a diagnostic catheter, allowing blood resistivity to be more easily and accurately measured. The cell comprises generally cylindrical body having an internal longitudinal bore of a known cross-sectional area and extending through the wall of the body are first and second pairs of longitudinally aligned electrodes. By joining a syringe to the proximal end of the assembly, a known volume of blood can be drawn into the cell. By applying an alternating current driving signal across the two outer electrodes and measuring the resistance between the two center electrodes, the blood's resistivity can be measured using the equation $\rho = AR/1$. By connecting the cell directly to the vascular catheter, the need to maintain the blood sample at body temperature is alleviated.

5 Claims, 1 Drawing Sheet

FLOW-THROUGH RESISTIVITY CELL

BACKGROUND OF THE INVENTION

1. Field of the Invention:

This invention relates generally to biomedical apparatus and more particularly to a flow-through resistivity cell attachable to a vascular diagnostic catheter for facilitating the measurement of blood resistivity.

2. Discussion of the Prior Art:

In certain diagnostic procedures, it is desirable to accurately determine the volume of a cardiac chamber. As is fully set out in the Salo et al Patent 4,686,987 and the Salo Patent 4,674,518, a technique called impedance plethysmography can be used to determine the ventricular volume of the heart. In making this measurement and computing this volume, a parameter which must be known is the resistivity of the patient's blood. In measuring resistivity, a sample of the patient's blood would first be drawn into a syringe and then transferred to a separate resistivity measuring cell of a known geometry where a resistance measurement would be taken. It is found, however, that the resistance measurement varies radically with temperature and that some means must be provided whereby the sample can be maintained at body temperature. An electrical heating element controlled by a body temperature measurement from a thermometer may be used. A delay is involved in waiting for the heater to bring the blood sample to body temperature, by slowing down the process and precluding real-time determination of chamber volume.

It is the principal object of the present invention to simplify the foregoing blood resistivity measurement apparatus and method so as to allow a rapid and accurate measurement of the blood resistivity to be taken, allowing a real-time computation of chamber volume.

SUMMARY OF THE INVENTION

In accordance with the present invention, a molded plastic tube of a known inside diameter and having four "dot" electrodes flush with the internal wall thereof is attached to the proximal end of a diagnostic catheter. The four electrodes are connected to an impedance measuring circuit in which a sine wave oscillator constant current source is connected across the two outermost electrodes and a measurement is taken of the voltage developed across the two innermost electrodes. This voltage is proportional to the resistivity of the fluid in the cell.

Because the cell is coupled directly to the proximal end of the diagnostic catheter, when a blood sample is drawn into the cell, it will be at body temperature. Because of the speed at which the measurements are taken, there can be no appreciable cooling of the blood sample. Moreover, because the resistivity cell of the present invention is coupled directly to the end of the diagnostic catheter, the fluid sample can be drawn through the module without disconnecting the catheter from the usual pressure monitoring equipment which may be involved in the diagnostic procedure.

DESCRIPTION OF THE DRAWINGS

The foregoing objects and advantages of the invention will become apparent to those skilled in the art from the following detailed description of the preferred embodiment, especially when considered in conjunction with the accompanying drawings in which like numerals in the several views refer to corresponding parts.

DESCRIPTION OF THE PREFERRED EMBODIMENT

Figure 1:
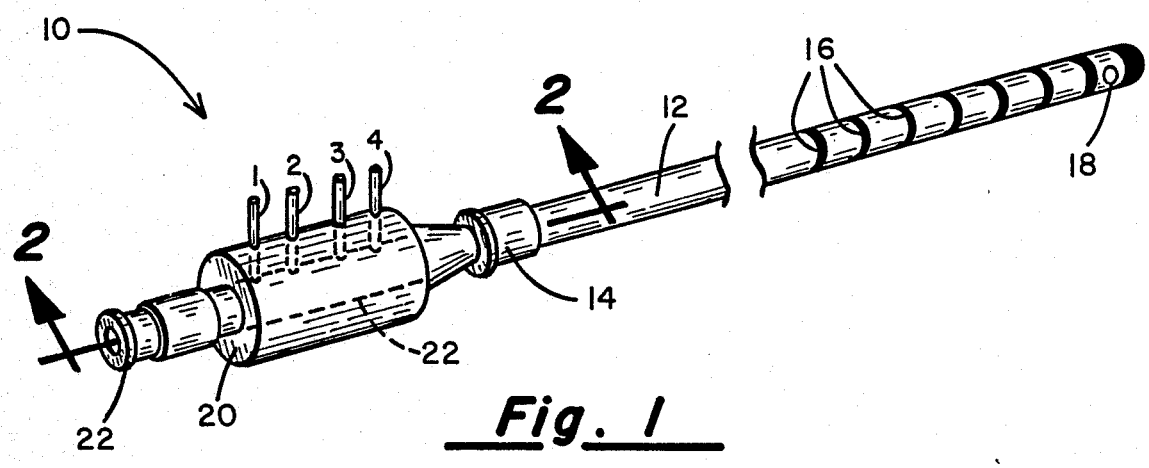
FIG. 1 is a perspective view of the proximal end portion of the diagnostic catheter showing the resistivity cell of the present invention.
Figure 2:
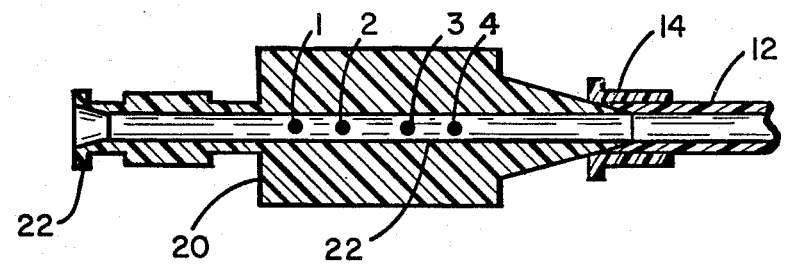
FIG. 2 is a cross-sectional view of the resistivity cell showing its internal construction.

Referring first to FIG. 1, there is indicated generally by numeral 10 a resistivity cell in accordance with the present invention. It is shown as being secured to the proximal end of a diagnostic catheter 12 by means of a luer fitting 14. The catheter 12 may be of the type described in the aforereferenced Salo Patent 4,674,518 in that it includes a plurality of spaced-apart ring electrodes 16 located near the distal end portion thereof. It is an elongated, flexible, tubular catheter having one or more ports as at 18 formed through the wall thickness of the catheter body and communicating with the lumen thereof.

The resistivity cell 10, itself, comprises a molded, rigid, plastic body 20 having a longitudinal bore 22 formed therethrough of a known cross-sectional area. Extending through the wall of the body 20 and terminating flush with the surface of the bore 22 are a plurality of electrodes labeled 1 through 4. The longitudinal spacing between electrodes is also a known factor.

Integrally molded with or otherwise joined to the proximal end of the cell body 20 is a female luer fitting 23. The fitting 23 is adapted to cooperate with a male fitting on the end of a plunger syringe or other source of negative pressure.

Electrodes 1 and 4 are the drive electrodes and are adapted to be connected to a sinusoidal constant current voltage source (not shown). Electrodes 2 and 3, in turn, are connected to a voltage measuring circuit also not shown. When used, the plunger on the syringe is drawn backward causing the patient's blood to flow through the distal port 18 and through the lumen of the catheter 12 and ultimately into the resistivity measuring cell 10. With blood filling the chamber 22, it will be in contact with the surface electrodes, allowing a measurement of the voltage developed across electrodes 2 and 3 occasioned by the application of the constant current source across electrodes 1 and 4. The voltage across the terminals 2 and 3 is proportional to the resistance of the blood in the cell. Knowing this resistance value, the resistivity of the blood may be computed using the formula $\rho = AR/l$ where A is the cross-sectional area of the bore 22, $l$ is the distance between electrodes 2 and 3 and R is the resistance of the blood sample.

Because the resistivity cell is directly connected to the proximal end of the catheter 12 which is routed through the vascular system, the blood sample drawn into the chamber 22 is at the patient's body temperature. That is to say, it does not have sufficient time to cool prior to the instant at which the resistance measurement is taken.

By way of example, and with no limitation intended, the electrodes 1 through 4 may be spaced 0.1 inches apart along the length of the body 20 and, typically, the diameter of the bore 22 may be about 4 mm. The body 20 may be molded from any number of suitable medical grade plastics, such as Lexan TM polycarbonate, PET or polybutylene terphalate (PBT).

Figure 3:
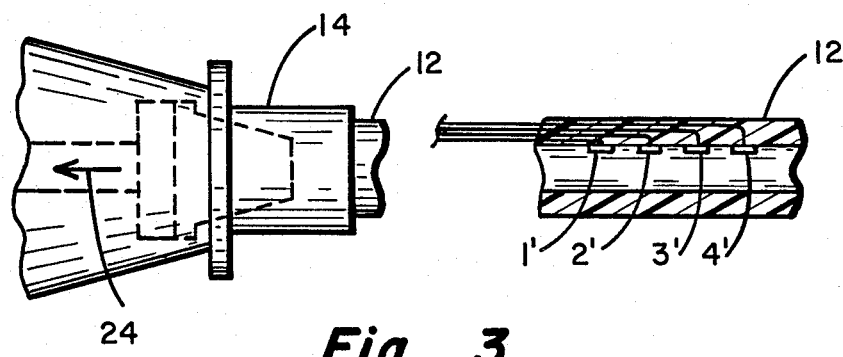
FIG. 3 illustrates an alternative embodiment.

Referring to FIG. 3, it is also contemplated that the electrodes 1' through 4' might also be placed on the interior wall surface of the catheter 12 with electrical conductors being routed to the proximal end of the catheter, either through the lumen thereof or by being embedded in the catheter wall. This would eliminate the need for a separate cell of the type shown in FIG. 1 while allowing the resistivity measurement to be taken on a flow-through basis when the syringe plunger 24 is retracted to draw blood therethrough. It is important that the electrodes be disposed within a section of the flexible catheter 12 where no deformation is likely to occur in that it is important to the computation that the cross-sectional area of the longitudinal segment between the electrodes 1' and 4' be known.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A blood resistivity measuring apparatus comprising:
   (a) cell means disposed along the length of a tubular intravascular catheter and having an internal chamber of known dimensions for intermittently and statically containing a predetermined volume of a patient's blood being drawn through said catheter, said cell means including a plurality of electrodes longitudinally spaced from one another and exposed to the interior of said chamber, means for applying a sinusoidal constant current signal across a predetermined pair of said plurality of electrodes for allowing the impedance of the blood between a further pair of said plurality of electrodes intermediate said predetermined pair to be measured, in situ.

2. The blood resistivity measuring apparatus as in claim 1 wherein said cell means is removably attached to said catheter.

3. The blood resistivity measuring apparatus as in claim 2 wherein said cell means comprises: a body member having an internal longitudinal bore of uniform cross-section extending the length of said body member with means for coupling said body member to the proximal end of said tubular catheter, said plurality of electrodes including first, second, third and fourth conductive pins extending through said body member so that the end surfaces thereof communicate with said longitudinal bore at predetermined longitudinally spaced locations along said bore.

4. The blood resistivity measuring apparatus as in claim 4 and further including means for drawing blood from the patient's body through said catheter to at least momentarily completely fill said longitudinal bore with a blood sample whose resistivity is to be measured.

5. The blood resistivity measuring apparatus as in claim 1 wherein said cell means is integral with said catheter.

* * * * *